United States Patent [19]

Klieman et al.

[11] Patent Number: 4,611,595
[45] Date of Patent: Sep. 16, 1986

[54] SPRING ACTIVATED HEMOSTATIC CLIP APPLICATOR

[75] Inventors: Charles H. Klieman, 3737 E. Century, Lynwood, Calif. 90262; Richard M. Densmore, Fountain Valley, Calif.

[73] Assignees: Charles H. Klieman, Lynwood; L. David Covell, Los Angeles, both of Calif.

[21] Appl. No.: 621,150

[22] Filed: Jun. 18, 1984

Related U.S. Application Data

[63] Continuation of Ser. No. 456,549, Jan. 10, 1983, abandoned, which is a continuation of Ser. No. 231,976, Jan. 6, 1981, abandoned, which is a continuation-in-part of Ser. No. 183,360, Sep. 2, 1980, Pat. No. 4,325,376, which is a continuation of Ser. No. 822,076, Aug. 5, 1977, abandoned.

[51] Int. Cl.[4] .................... A61B 17/04; A61B 17/12; B31B 1/00
[52] U.S. Cl. .................. 128/334 R; 227/DIG. 1; 227/19; 128/325; 128/326
[58] Field of Search .............. 128/325, 326, 334 R; 227/19, 119, DIG. 1

[56] References Cited

U.S. PATENT DOCUMENTS

| | | | |
|---|---|---|---|
| 4,152,920 | 5/1979 | Green | 128/325 |
| 4,166,466 | 9/1979 | Jarvik | 128/325 |
| 4,242,902 | 1/1981 | Green | 128/325 |
| 4,430,997 | 2/1984 | DiGiovanni et al. | 128/326 |

FOREIGN PATENT DOCUMENTS 0086721 8/1983 European Pat. Off. .
2088723 6/1982 United Kingdom .

Primary Examiner—Gene Mancene
Assistant Examiner—C. W. Shedd
Attorney, Agent, or Firm—Spensley Horn Jubas & Lubitz

[57] ABSTRACT

A surgical clip applying device having a main body, a clip magazine coupled to the exterior of the main body for holding a plurality of clips, clip deforming jaws coupled to the main body for receiving and deforming clips, a clip feed blade for moving clips from the clip magazine to the deforming jaws, and a spring activated actuating mechanism. The actuating mechanism includes handle portions, a ratchet member connected to the handle portions, a spring connected to the main body and the ratchet member, along with a latch adapted to engage the ratchet member. By movement of one of the handle portions with respect to the other handle portion energy is stored in the spring and retained therein via engagement of the latch with the ratchet member. In operation, a slight movement of one of the handle portions with respect to the other handle portion disengages the latch from the ratchet member so that the energy stored in the spring is converted into rapid forward movement of the clip feed blade. This forward movement causes the clip feed blade to slide through the magazine and rapidly place a clip in the deforming jaws.

27 Claims, 11 Drawing Figures

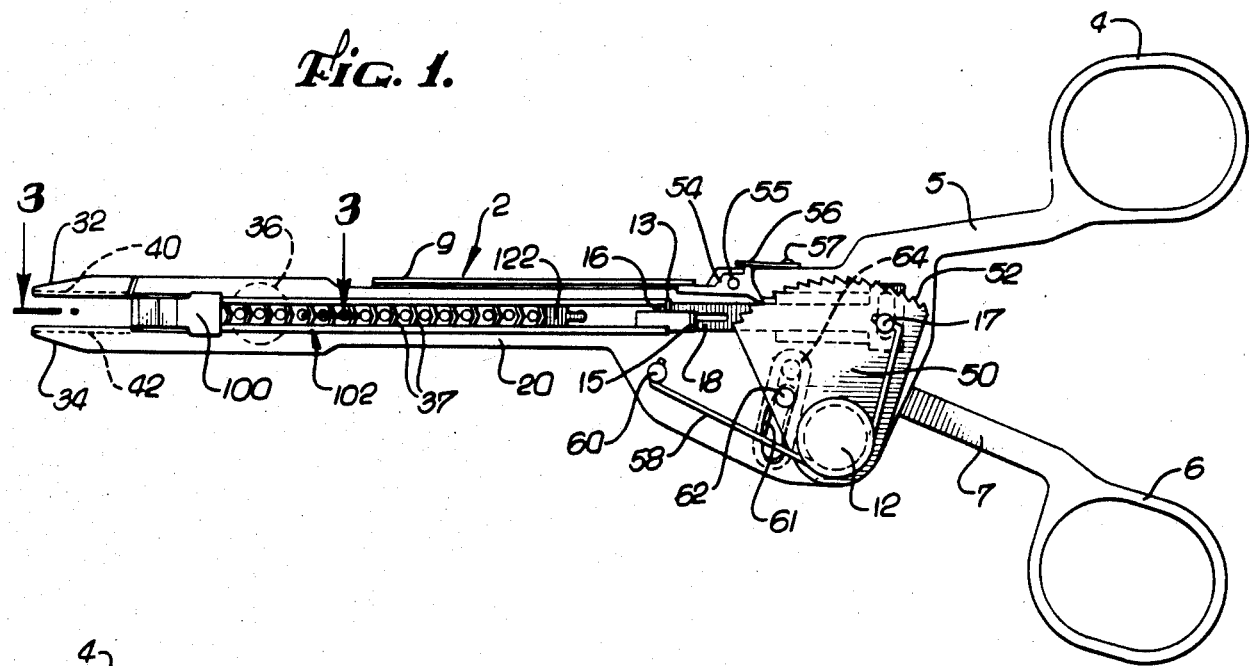

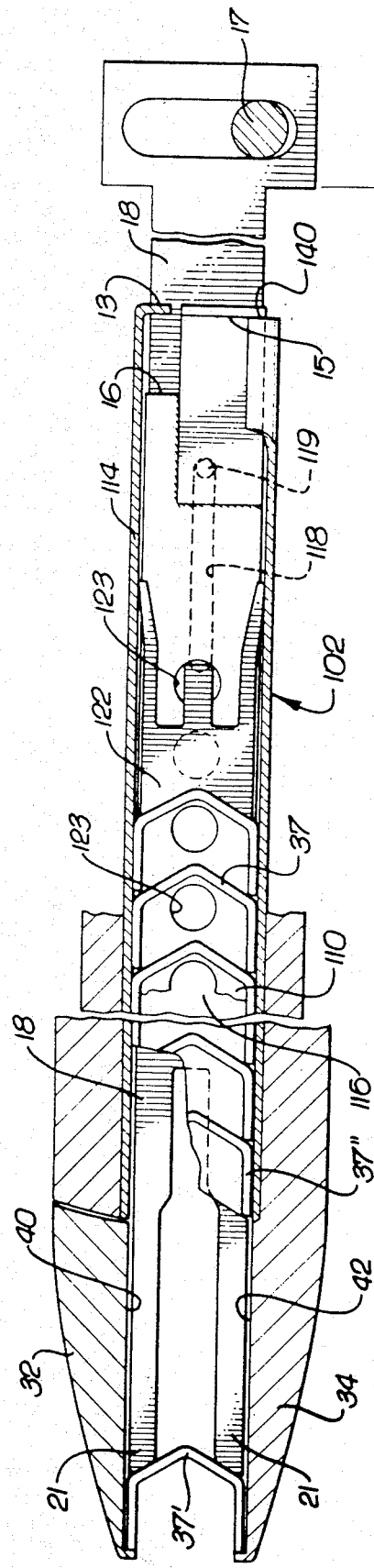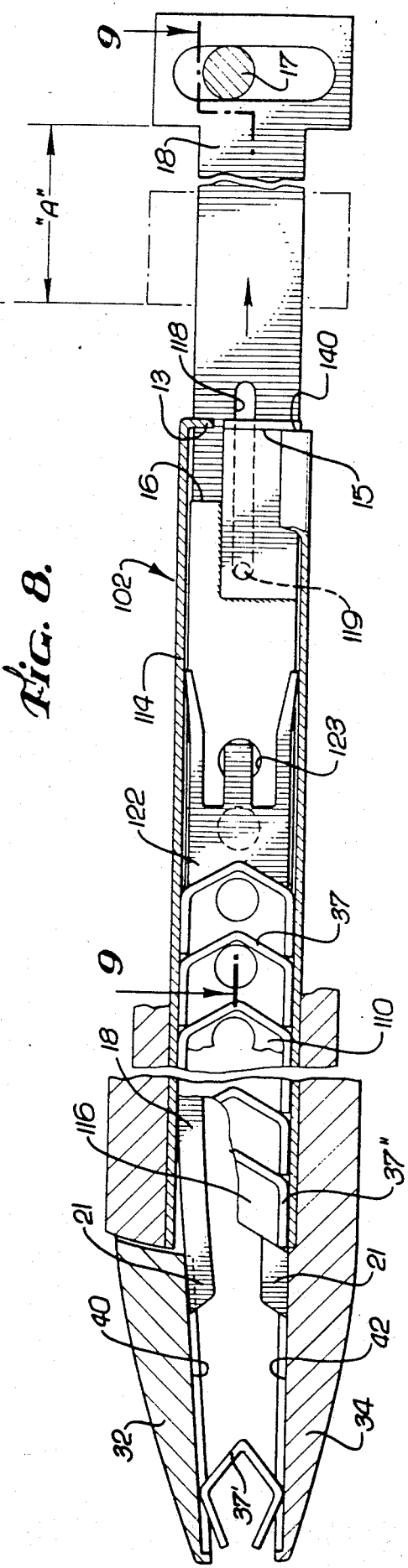

SPRING ACTIVATED HEMOSTATIC CLIP APPLICATOR

BACKGROUND OF THE INVENTION

Patent Applications

This application is a continuation of application Ser. No. 456,549 filed Jan. 10, 1983, now abandoned, which is a continuation of application Ser. No. 231,976 filed Jan. 6, 1981, now abandoned, which is a continuation in part of application Ser. No. 183,360 filed Sept. 2, 1980, now U.S. Pat. No. 4,325,376, which is a contination of application Ser. No. 822,076 filed Aug. 5, 1977, now abandoned.

In U.S. Pat. No. 4,188,953 entitled Hemostatic Clip, issued on Feb. 19, 1980, and assigned to the present assignee, hemostatic clips adapted for utilization in the present invention and similar devices is disclosed.

In the above-referenced copending U.S. Patent Application entitled Hemostatic Clip Applicator, and assigned to the present assignee, a Hemostatic Clip Applicator for the strangulation of tubular members in a rapid and automatic manner is disclosed. That application is directed, in part, to a device having a main body, a clip cartridge, actuating handles, and clip deforming jaws. Disposed within the clip cartridge are a plurality of hemostatic clips, and a clip feed means which moves clips to the clip deforming jaws where the clips are deformed about a blood vessel or the like.

While the applicator noted in the preceding paragraph provides a novel method for automatically closing blood vessels and other fluid ducts, it requires the manual feeding of a hemostatic clip into the deforming jaws by the forward movement of one of two handles. That is, to operate that device, the surgeon must first move one of the handle portions to a forward position so as to load a hemostatic clip in the deforming jaws, and then return that handle portion to its neutral position. Once the surgeon has located the hemostatic clip around the tubular member to be closed, he squeezes both handle portions together resulting in the crimping of a clip about the blood vessel. When the surgeon is ready to close another blood vessel, this same sequence of moving one handle portion forward and then rearward must be repeated so as to sequentially load and close a clip.

It is toward the refinement of the device disclosed in the copending U.S. patent application noted above that the present invention is directed, and more specifically, toward a device which rapidly, yet almost effortlessly, loads a hemostatic clip in the deforming jaws of the instrument.

FIELD OF THE INVENTION

The invention relates to the field of devices useful in the application of hemostatic clips, and more specifically, to devices for the application of hemostatic clips used in the strangulation of blood vessels and other fluid ducts.

PRIOR ART

In a typical surgery procedure, a great many veins, arteries, and other blood vessels must be severed and closed. This is often a difficult and time consuming procedure since many vessels are located in obscure areas where there is little room in which to work. Thus, it is apparent that a device which would reduce the time required for closure of blood vessels would be a great benefit to both surgeon and patient.

One prior art attempt to provide a device which can more rapidly close a blood vessel is disclosed by Jarvik, U.S. Pat. No. 4,146,466. The Jarvik device has a channel in the main body of the instrument which is integral with one of the jaws of the instrument. In the Jarvik device, a clip pusher moves the lower most clip in a clip stack through the channel in the main body to the jaws at the far end of the instrument. However, the pusher does not enter the jaws of the Jarvik instrument, but merely abuts the aftmost portion of the jaws without sliding therebetween. In addition, upon application of the hemostatic clip by the Jarvik instrument, the pusher is positively prevented from returning from its farthest most position. Most importantly, the Jarvik patent does not disclose an instrument which utilizes a spring loaded mechanism so as to move rapidly and accurately a clip from an internal clip magazine to the jaw portions of the instrument.

Another prior art attempt to provide a device which can more rapidly close a blood vessel is disclosed by Wood, U.S. Pat. No. 3,326,216. The Wood device consists of a hemostat-like instrument which has finger loop portions coupled to jaw portions. The jaw portions are adapted to hold a hemostatic clip therebetween so that the clip may be closed about a vessel by bringing the finger loops together. Wood also discloses a separate cartridge which holds a plurality of clips. When the Wood device is to be used, the jaw portions are placed about one clip contained in the cartridge and the clip is removed from the cartridge by the engagement of the clip by the jaw portions. When the clip has been used, a new clip may be placed in the instrument by returning to the clip cartridge and manually inserting a new clip. Two problems are apparent with the Wood device. First, hemostatic clips are not automatically and rapidly fed into the jaws of the device, but must be individually placed there. This procedure is time consuming and cumbersome. In addition, the Wood device is capable of expanding its jaws wider than the width of a clip contained therein. Thus, a clip may be accidentally dropped from the device causing a great deal of inconvenience and delay.

A third prior art attempt to provide more rapid yet effective strangulation of blood vessels and the like is described by Miles, U.S. Pat. No. 3,082,426. Miles discloses a surgical stapling device which consists of finger loops coupled to a pair of arms which terminate in jaw portions, the jaw portions being adapted to grasp and hold a tubular member. The Miles device also has a magazine holding a plurality of clips along the length of one arm, and manually operable clip ejector means for placing a clip about the tubular member which is to be closed. In operation, a tubular member is first grasped and held by the jaw portions of the Miles device. The surgeon then places his index finger on the button attached to the clip ejector. By urging the button forward, the clip ejector places a clip about the tubular member. Then, the clip may be deformed about the blood vessel by bringing the pair of finger loops together.

An obvious disadvantage of the Miles device is that it is cumbersome, in that the surgeon must manually move a clip between the jaws of the device while holding the device steady so as not to loose the grasp of the tubular member. Also, this procedure is time consumming in that each individual clip must be manually fed between the jaws of the stapling device.

Accordingly, it is a general object of the present invention to provide an improved hemostatic clip applicator device for the strangulation of blood vessels and the like.

It is another object of the present invention to provide an improved hemostatic clip applicator device which rapidly and automatically feeds clips to its forward portion and then provides deformation of the clips about blood vessels.

It is yet another object of the present invention to provide an improved hemostatic clip applicator device which provides high visibility to the user.

SUMMARY OF THE INVENTION

A hemostatic clip applicator device useful for rapidly and automatically applying clips for the strangulation of blood vessels and the like is provided. The device has a clip magazine coupled to the exterior of a main body, the clip magazine being adapted to hold a plurality of hemostatic clips. Attached to one end of the main body are clip deforming jaws adapted to hold and crimp a hemostatic clip about a blood vessel. Slideably disposed within the clip magazine is a clip feed means which is adapted to move clips from the magazine to the clip deforming jaws. Coupled to the clip feed means and the clip deforming jaws is an actuating means. The actuating means includes handle portions coupled to the main body and an energizing means coupled to the main body, the clip feed means, and the handle portions. The energizing means is adapted to store energy and selectively supply that energy to the clip feed means.

By a slight outward movement of the handle portions, the energizing means is activated to supply the stored energy to the clip feed means so as to cause one of the clips stored in the clip magazine to be moved rapidly to the clip deforming jaws. Once located in the clip deforming jaws, the clip can be crimped about a blood vessel or the like simply by squeezing the handle portions toward one another. As a consequence of this squeezing of the handle portions toward one another, energy is again stored in the energizing means so as to be available for a subsequent rapid placement of a clip in the deforming jaws. This sequence of rapidly feeding clips to the clip deforming jaws and crimping them, may be repeated until the plurality of clips located in the clip magazine is depleted.

The novel features which are believed to be characteristic of the invention, both as to its organization and its method of operation, together with further objects and advantages thereof, will be better understood from the following description in connection with accompanying drawings in which a presently preferred embodiment of the invention is illustrated by way of example. It is to be expressly understood, however, that the drawings are for the purpose of illustration and description only and are not intended as a definition of the limits of the invention.

BRIEF DESCRIPTION OF THE DRAWINGS

FIG. 1 is a side view of the clip applicating device of the present invention;

FIG. 2 is a side view of the back side of the clip applicating device of the present invention;

FIG. 3 is an enlarged cross-sectional view of the forward section of the present invention taken along the lines 3—3 of FIG. 1;

FIG. 6 is an enlarged cut-away view of the instrument of the present invention taken along the lines 6—6 of FIG. 5;

FIG. 8 is a top cut-away view of the instrument of the present invention in its configuration as illustrated in FIG. 7;

DETAILED DESCRIPTION OF THE INVENTION

Figure 4:
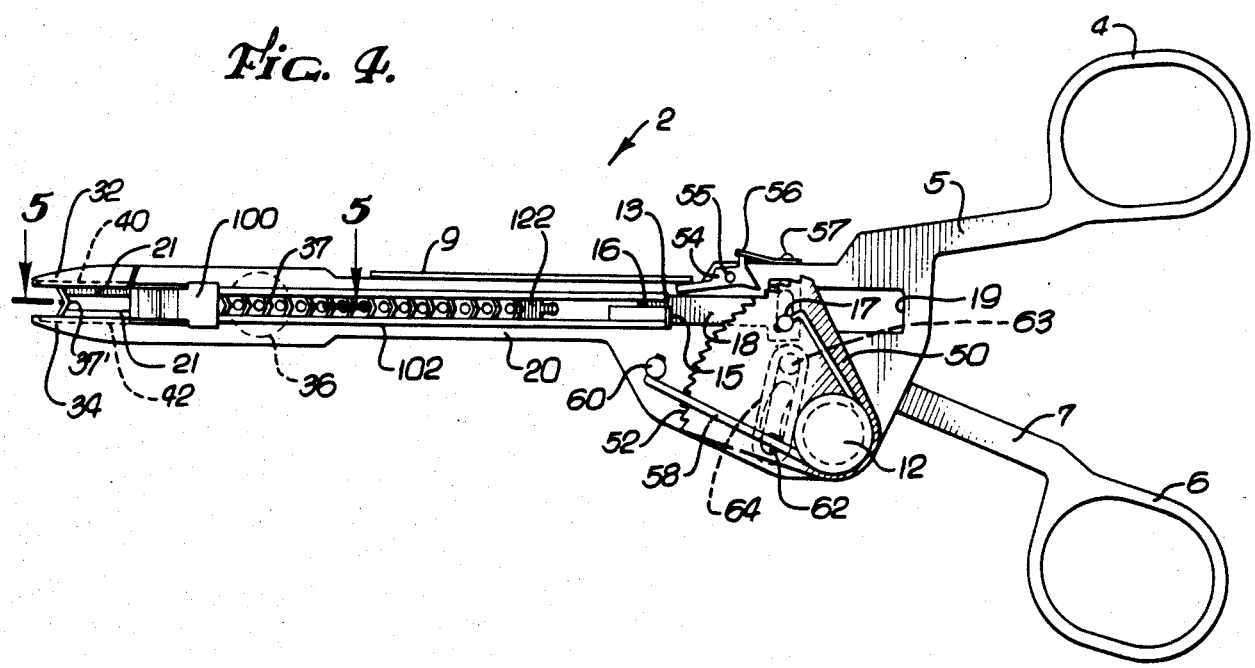
FIG. 4 is a side view of the clip applicating device of the present invention in its configuration immediately following the rapid loading of a clip into the jaws of the device.

A spring activated hemostatic clip applicator device is disclosed which is useful in rapidly applying a sequence of hemostatic clips about blood vessels and other fluid ducts. The hemostatic clip applicator of the present invention may be used with hemostatic clips such as is described in our U.S. Pat. No. 4,188,953 issued on Feb. 19, 1980, entitled "Hemostatic Clip", or with any other suitably adapted hemostatic clip.

Referring to FIG. 1, the spring activated hemostatic clip applying device 2 of the present invention is shown with its actuating means in its "cocked" configuration. The actuating means is comprised of an energizing means, and handle portions. In the presently preferred embodiment, the energizing means is comprised of ratchet member 50, ratchet spring 58, and latch 54. The upper handle portions are comprised of an upper finger loop 4 and upper finger loop member 5, along with lower finger loop 6 and lower finger loop member 7. Upper finger loop 4 and upper finger loop member 5 are integral with main body 20.

As will be more fully described hereinbelow, clip feed blade 18 is a clip feed means which in the presently preferred embodiment is a blade member adapted to slide rapidly through clip magazine means 102 and into the forward portions (i.e., those portions to the left of FIG. 1) of device 2. Also, as will be described more fully hereinbelow, the rapid movement of clip feed blade 18 into the forward portions of device 2, and the corresponding movement of a hemostatic clip 37 into the jaw members 32, 34 of device 2, is accomplished merely by activating the energizing means of the present invention.

Disposed within clip magazine means 102 are a plurality of hemostatic clips 37, and magazine 102 is adapted such that the individual clips are available to be moved forward by clip feed blade 18. Spring guide means 100 aid the movement of a clip from magazine 102 into the main body 20 of instrument 2.

Coupled to the forward portion of main body 20 is a clip deforming means adapted to deform a hemostatic clip 37 about a blood vessel or the like. In the presently preferred embodiment, the clip deforming means is comprised of upper jaw portion 32 and lower jaw portion 34. Upper jaw portion 32 is fixedly coupled to lower finger loop member 7 and pivotally coupled to main body 20 by upper jaw pivot 36, while lower jaw portion 34 is fixedly coupled to main body 20. When a hemostatic clip 37 has been fed from the clip magazine 102 into grooves 40 and 42 of jaw portions 32 and 34 by the interaction of clip feed blade 18 and the energizing means, the clip may be squeezed about a blood vessel by squeezing finger loops 6 and 4 together so that upper jaw portion 32 closes toward lower jaw portion 34.

Now referring more particularly to the energizing means of the present invention, reference is made to the main components of the energizing means—ratchet member 50, latch 54, latch spring 56, and ratchet spring 58. As illustrated in FIG. 1, ratchet member 50 is coupled to clip feed blade 18 by means of pin 17, while lower finger loop 6 is coupled to ratchet member 50 by ratchet pin 62. Furthermore, one end of ratchet spring 58 is coupled to main body 20 by pin 60, while the other end is coupled to ratchet member 50 and feed blade 18 by pin 17. In the configuration illustrated in FIG. 1, energy has been stored in ratchet spring 58, that energy being directed toward the counter-clockwise rotational movement of ratchet 50 and the corresponding forward movement of clip feed blade 18. Energy remains stored in spring 58 because counter-clockwise rotational movement of ratchet 50 is prevented by the engagement of latch 54 with the teeth 52 of ratchet 50. Latch 54 is held in engagement with ratchet 50 by the urging of spring 56, that spring being coupled to main body 20 by rivet 57. In the presently preferred embodiment ratchet spring 58 is a helical spring, although other types of springs could be readily utilized.

In operation, a slight movement of upper finger loop 4 away from lower finger loop 6 causes lower finger loop member tab portion 9 to rotate latch 54 about pin 55 in a counter-clockwise direction. This counter-clockwise rotation of latch 54 causes latch 54 to disengage from the teeth 52 of ratchet 50. With the removal of the impediment of latch 54, ratchet spring 58 is free to cause a counterclockwise rotational movement of ratchet member 50 about its pivot point 12. This rotational movement ratchet member 50 causes clip feed blade 18 to rapidly advance through the instrument and thereby immediately place a hemostatic clip 37 in the extreme ends of jaw portions 32, 34. As will be explained in more detail hereinbelow, the forward advance of clip feed blade 18 is controlled and fixed by the abutment of forward stop 15 with magazine 102. Similarly, the rearward reach of clip feed blade 18 is controlled by the abutment of rearward stop 16 with end tab 13 of magazine 102.

It is important to note from FIG. 1 that the outward movement of upper jaw portion 32 is limited by the abutment of main body 20 of instrument 2 with finger loop member tab portion 9. Thus, if a hemostatic clip is located in jaw portions 32 and 34, it may not accidentally be dropped by the over expansion of upper jaw 32 with respect to lower jaw 34.

FIG. 2 is a view of the reverse side of the spring activated clip applying device 2. Shown in this view is the relationship of lower finger loop 6 and lower finger loop member 7 with main body 20 and upper jaw portion 32. The lower finger loop member 7 is fixedly secured to upper jaw portion 32, while the combination of lower finger loop 7 and jaw portion 32 are pivotally coupled to main body 20 by upper jaw pivot 36. It can be seen that maximum outward travel of lower finger loop 6, and thus the maximum expansion of upper jaw portion 32, is limited by the abutment of lower finger loop tab portion 9 with main body 20.

Also illustrated in FIG. 2, is the relationship of link 64, ratchet pin 62, link pin 63, and the slot 61 in main body 20. In the condition illustrated in FIGS. 1 and 2, lower finger loop 6 is free to travel inwardly and outwardly about pivot 36 within the confines of the travel of ratchet pin 62 within the slot 59 in link 64. This freedom of movement of lower finger loop 6, and the corresponding freedom of movement of upper jaw portion 32 with respect to lower jaw portion 34 has the following very useful advantage during a surgery. If a hemostatic clip 37 has been previously applied to a blood vessel or the like during surgery, and it becomes necessary to further crimp or secure that hemostatic clip 37, the freedom of movement of instrument 2, as illustrated in FIGS. 1 and 2, allows the surgeon to place the previously crimped hemostatic clip 37 between jaws 32 and 34 and make further crimping adjustment as necessary.

Finally, in reference to FIG. 2, it can be seen that pin 17, which couples ratchet 50 to feed blade 18, is free to move through window 19 in main body 20. Thus, when the energizing means induces a forward movement of feed blade 18, pin 17 can freely travel from left to right in window 19. Correspondingly, the rearward movement of feed blade 18 is stopped by the abutment of pin 17 with the end of window 19.

FIG. 3 is a top cross-sectional view of the forward portion of clip applying device 2, as taken through lines 3—3 of FIG. 1. In the forward most portion of FIG. 3, it can be seen that there is a groove 42 disposed within lower jaw portion 34. Groove 42 in conjunction with the corresponding groove 40 in upper jaw portion 32 serves to guide and secure a hemostatic clip 37 as it is rapidly moved from the main body 20 of instrument 2 to the forward most portions of jaws 32, 34.

FIG. 3 also illustrates in greater detail the components comprising the clip magazine 102 and the clip feeding means of the present invention. Clip magazine 102 is comprised of a magazine housing 114, containing a plurality of hemostatic clips 37. Located within clip magazine housing 114 is ratchet bar 110 and just below ratchet bar 110 is platform blade 116. Furthermore, just between housing 114 and platform blade 116 is clip feed blade 18.

It can be seen from FIG. 3 that the forward movement of clip feed blade 18 through magazine 102 will move hemostatic clip 37' from its key position 125 through lower jaw portion groove 42 and ultimately to the extreme end of lower jaw portion 34. As illustrated in FIG. 3, jaw portions 32 and 34 can be curved away from main body 20 to allow better visibility during usage. Thus, feed blade 18 must be configured so as to be capable of being moved forward through grooves 40 and 42 while simultaneously bending away from main body 20 in grooves 40 and 42. In the presently preferred embodiment, this capability has been provided by constructing feed blade 18 of three layers of thin blades of metal in a laminated configuration. The three layers are only coupled to discreet points so that the feed blade 18 is able to move longitudinally through magazine 102 while curving around grooves 40 and 42 in jaw portions 32 and 34.

It can also be seen in FIG. 3 that guide spring means 100 is adapted to maintain clip 37' in its key position 125 until clip 37' is moved forward by feed blade 18. In addition, leaf spring 112 is adapted to maintain clip 37" in its proper position so that it is available to be moved into key position 125 so as to replace clip 37'. Leaf spring 112 is adapted to fit between the arms of clip 37' while securing the clip at its bail portion, and thus maintain clip 37' in a flat orientation with respect to housing 114. This secured orientation prevents feed blade 18 from inadvertantly slipping under clip 37'. Furthermore, the pressure exerted by spring 112 on the bail portion of clip 37' ensures that all clips 37 remain properly positioned during the loading sequence. It can also be seen in FIG. 3 that clip magazine 102 is comprised of a simply constructed housing 114 which, in the presently preferred embodiment, is spot welded to main body 20. This method of forming and attaching the magazine 102 allows housing 114 to be inexpensively stamped from stock material and then attached to the main body 20. Of course, clip magazine 102 can be replaceably coupled to main body 20 so that when the clips 37 are depleted from magazine 102, that magazine 102 can be removed from instrument 2 and a new magazine 102 can be placed therein.

Now turning to FIG. 4, instrument 2 is illustrated in its configuration just following the spring activated loading of hemostatic clip 37' into jaw portions 32, 34. As noted in the discussion of FIG. 1, a slight upward movement of finger loop 4 with respect to finger loop 6 causes lower finger loop member tab portion 9 to abut and thereby rotate latch 54 in a counter-clockwise direction so as to disengage latch 54 from teeth 52 of ratchet member 50. Immediately after this disengagement of latch 54 from ratchet member 50, the energy stored in ratchet spring 58 causes ratchet member 50 to rotate about pivot point 12, and thereby rapidly move clip feed blade 18 through magazine 102, and ultimately move hemostatic clip 37' into jaw portions 32, 34. This rapid forward movement of clip feed blade 18 is brought to an abrupt halt, by the abutment of forward stop 15 with magazine 102, at just the point where clip 37' is properly positioned in jaws 32, 34.

It should be particularly noted in FIG. 4 that the forward most end of clip feed blade 18 is comprised of two sections 21 which are arranged in a forked configuration. The abutment of forked ends 21 of clip feed blade 18 with the bail portion of hemostatic clip 37' provides the significant advantage of preventing rearward movement of clip 37' when the clip is being positioned around a blood vessel or the like. Furthermore, the forked configuration of the forward most end 21 of clip feed blade 18 has the significant advantage of not reducing visibility through jaw portions 32, 34.

Figure 5:
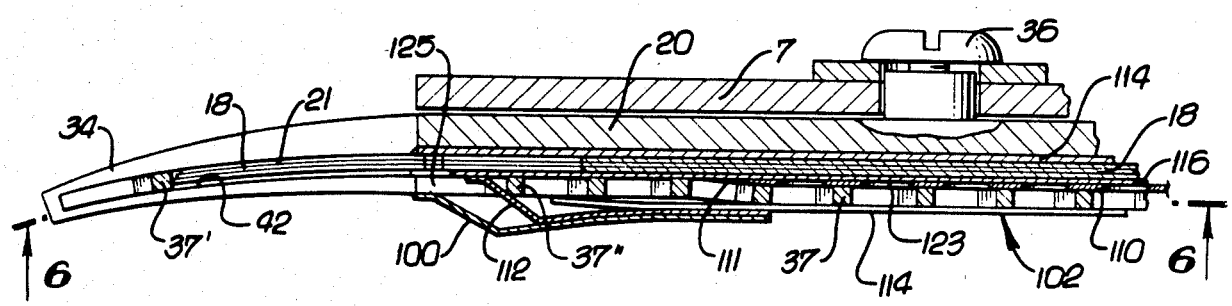
FIG. 5 is an enlarged top cross-sectional view of the forward portion of the instrument of the present invention taken along the lines 5—5 of FIG. 4.

FIG. 5 is a cross-sectional top view of the forward most section of clip applying device 2, taken along the lines 5—5 of FIG. 4. It can be seen in this figure that hemostatic clip 37' is located in the forward most position in lower jaw 34, and is held in that position by the abutment of clip feed blade 18. It can also be seen in FIG. 5 that another hemostatic clip 37" has now been moved into the key position 125 so as to be available during the next spring activated loading sequence. It is important to note that clip 37" is resting on platform blade 116 and held in place by guide spring 100 and leaf spring 112. Platform blade 116 prevents one or both legs of clip 37" from becoming disoriented within key position 125. It can also be seen that ratchet bar 110, in its forward most position, terminates substantially before the end of platform blade 116 and has a sloping forward portion 111 to guide additional clips 37 onto platform blade 116.

FIG. 6 is a cross-sectional cutaway view of instrument 2 taken along the lines 6—6 of FIG. 5. Thus, FIG. 6 illustrates in greater detail the relationship of platform blade 116, feed blade 18, and ratchet bar 110. The fork ends 21 of feed blade 18 can be seen abutting the bail portion of clip 37'. Disposed just above clip feed blade 18 is platform blade 116, on which is resting clip 37". Also shown in FIG. 6 is a ratchet bar 110 with its plurality of ratchet bar holes 123. Disposed in the rearwardmost ratchet bar hole 123 is pawl 122. It should also be noted in FIG. 6 that lost motion pin 119 is disposed in the rearward-most portion of lost motion slot 118 contained in feed blade 18.

FIG. 6 further illustrates the relationship of forward stop 15, rearward stop 16 and magazine housing 114. In the configuration illustrated in FIG. 6, the feed blade 18 has advanced to its forward most position and is prevented from any further forward movement by the abutment of forward stop 15 with the upper edge 140 of housing 114. It can also be seen that at the end of the maximum rearward movement of ratchet bar 110, rearward stop 16 will abut tab 13 of magazine housing 114 and thereby prevent any further rearward movement.

Figure 7:
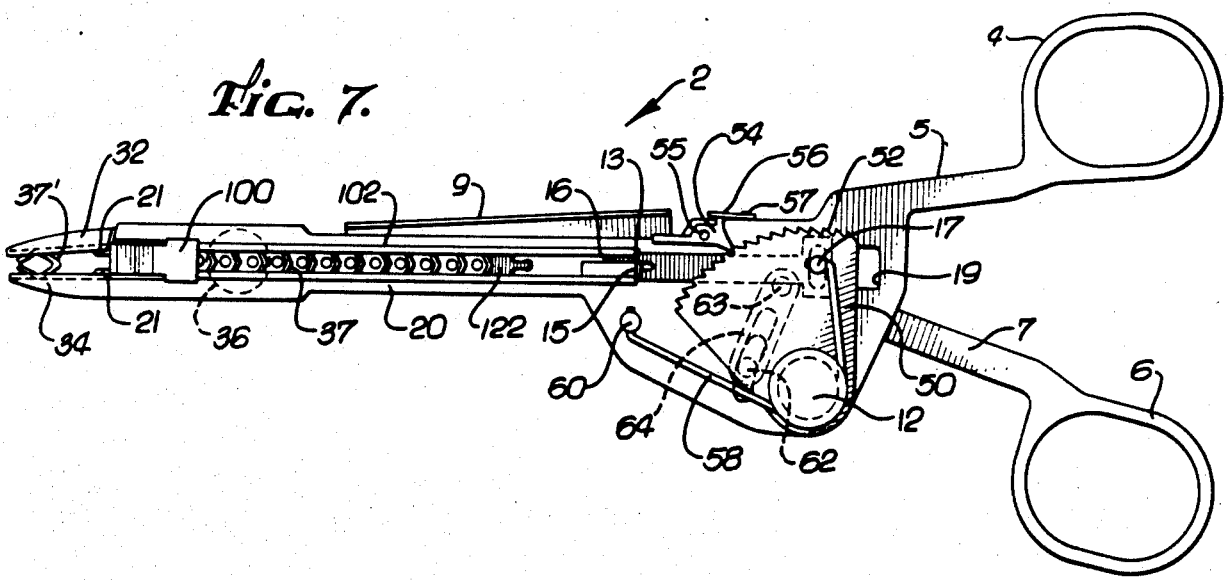
FIG. 7 is a side view of the clip applicating device of the present invention illustrating the simultaneous crimping of a hemostatic clip and the cocking of the clip feed mechanism.

Now turning to FIG. 7, the configuration of spring activated clip applying device 2 while a hemostatic clip 37' is being crimped is illustrated. Due to the movement of lower finger loop 6 toward upper finger loop 4, and the resulting pivoting of upper jaw 32 around pivot 36, upper jaw portion 32 is moved toward lower jaw portion 34 so as to crimp hemostatic clip 37'.

There are two important occurrences to be noted as the result of this crimping operation illustrated in FIG. 7. First, it can be seen that the forked ends 21 of feed blade 18 are simultaneously being retracted from jaw portions 32, 34 while being bent toward one another by the closing jaw portions 32, 34. Second, as lower finger loop 6 is moved toward upper finger loop 4, energy is again being stored in ratchet spring 58 by the rotation of ratchet member 50 about pivot point 12. This rotational movement of ratchet member 50 about pivot 12 is caused by the movement induced by link 64. As illustrated in FIG. 7, in phantom, link 64 is coupled to lower finger loop 7 via link pin 63. Thus, as lower finger loop 6 is moved upward, link 64 is also moved upward so as to cause an upward force to be applied to ratchet pin 62 and a corresponding rotation of ratchet member 50. That is, as finger loop 6 is lifted toward finger loop 4, pin 62 moves through slot 61 in main body 20 (see FIG. 2) and thus rotates ratchet member 50. This rotation causes a distortion of spring 58 and results in a storage of energy therein. Of course, any counter-clockwise movement of ratchet member 50 is prevented by the interaction of latch 54 with ratchet member 50. Because lower finger loop member tab portion 9 is no longer interacting with latch 54, and because latch spring 56 is causing a clockwise rotational movement of latch 54 about latch pivot 55, latch 54 is caught in one of the various ratchet teeth 52 disposed about the upper perimeter of ratchet member 50. As ratchet member 50 is rotated clockwise, latch 54 rides up and over each of the inclined teeth 52 of ratchet member 50 so as to continue to prevent counter-clockwise rotation of ratchet member 50. Of course, a variety of other mechanisms could be used in place of the ratchet member 50 and latch 54 so as to provide a releasable impediment to movement. For example, a frictional engagement mechanism could be used which would still provide a quick release action.

FIG. 8 illustrates in greater detail the relationship of feed blade 18, ratchet bar 110, and platform blade 116 when the instrument 2 is configured as illustrated in FIG. 7. In comparison with FIG. 6, it can be seen in FIG. 8 that clip feed blade 18 has moved a total rearward distance "A". This rearward movement has caused the forked ends 21 of clip feed blade 18 to retract from jaw portions 32, 34, and the bending of forked ends 21 toward one another as jaw portions 32 and 34 converge.

Further, comparison of FIGS. 6 and 8 will disclose that lost motion pin 119 has traveled the length of the lost motion slot 118 contained in feed blade 18. Because lost motion pin 119 is a part of platform blade 116 and is further coupled to ratchet bar 110, this rearward movement of pin 119 through lost motion slot 118 has resulted in no rearward movement of either platform blade 116 or ratchet bar 110. Of course, the further rearward movement of feed blade 18 will cause a corresponding rearward movement of both platform blade 116 and ratchet bar 110 due to the abutment of lost motion pin 119 with the forward most section of lost motion slot 118. Ultimately, further rearward movement will be prevented when stop 16 on ratchet bar 110 abuts rear stop 13. The prevention of additional rearward movement of ratchet bar 110 also prevents further rearward movement of feed blade 18 and platform blade 116 due to the coupling thereof by pin 119.

Figure 9:
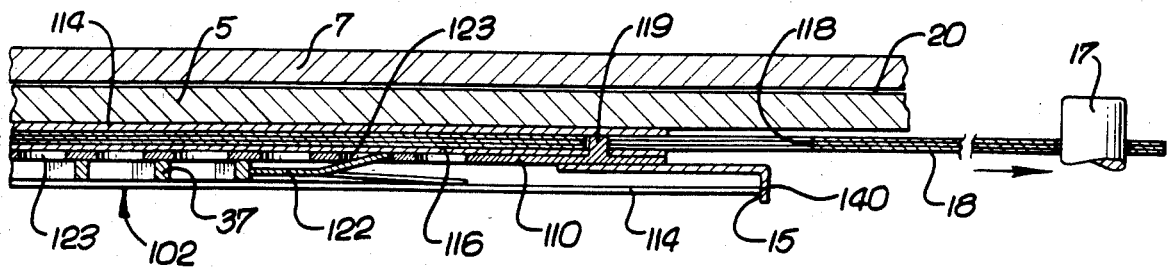
FIG. 9 is a cross-sectional view of the rearward sections of the instrument of the present invention taken along the lines 9—9 of FIG. 8.

FIG. 9 is a cross-sectional top view of a portion of the instrument illustrated in FIG. 8, taken along lines 9—9 of FIG. 8. In FIG. 9 it can be seen that clip magazine 102 is comprised of a magazine housing 114 which encloses clip feed blade 18, ratchet bar 110, platform blade 116, pawl 122, and a plurality of hemostatic clips 37. It can be seen in this figure that lost motion pin 119 has traveled the length of lost motion slot 118 and is now abutting the forward-most end of slot 118. Because pawl 122 is frictionally engaged with the sides of clip magazine housing 114 so as to oppose rearward movement, any further rearward movement of clip feed blade 18 will cause both platform blade 116 and ratchet bar 110 to move rearward, thereby causing pawl 112 to exit ratchet bar hole 123, travel along the surface of ratchet bar 110, and become disposed in the next ratchet bar hole 123'. Of course, a variety of other methods are available to prevent rearward movement of pawl 122, including the use of serrations in the interior of housing 114 in combination with spring tabs on pawl 122.

Figure 10:
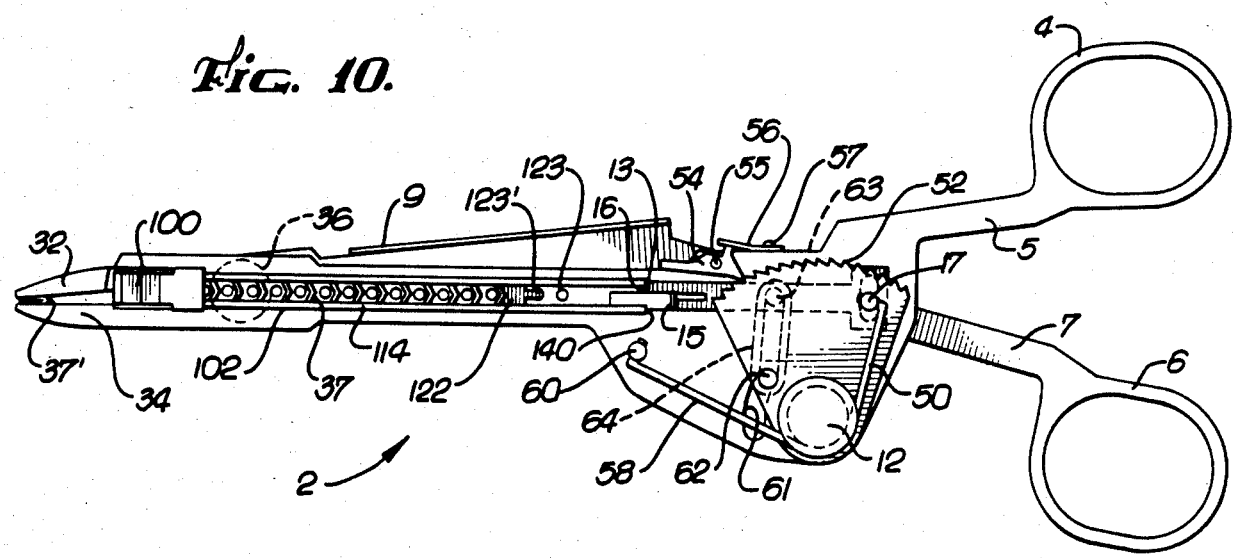
FIG. 10 is a side view of the clip applicating device of the present invention illustrating the device in its fully cocked position.

Now turning to FIG. 10, spring activated hemostatic clip applicator 2 is shown in its fully cocked position. Finger loop 6 has been brought as close as possible to finger loop 4, thereby causing upper jaw portion 32 virtually to abut lower jaw portion 34, and thereby completely crimp hemostatic clip 37'. This complete movement of lower finger loop 6 toward upper finger loop 4 has also caused the complete clockwise rotation of ratchet member 50 due to the lifting by link 64. As a consequence of the clockwise rotational force applied by latch spring 56, latch 54 continues to prevent the counter-clockwise rotational movement of ratchet 50. Thus, in this position, the energy has been restored in ratchet spring 58, so as to be available for subsequent instantaneous feeding of a hemostatic clip 37 into the jaws 32, 34. Of course, rearward stop 16 has again abutted the tab 13 of clip magazine 102 so as to prevent any further rearward movement of ratchet bar 110.

It is important to note in connection with FIG. 10 that pawl 122 has advanced from the rearward-most ratchet bar hole 123 to the next ratchet bar hole 123'. As explained more fully in Patent Application Ser. No. 822,076 the relative forward movement of pawl 122 has caused the series of clips 37 contained in magazine 102 to also move forward. This forward movement of pawl 122 and clips 37 has now placed a new clip in key position 125. Thus, this retraction of upper finger loop 4 and the convergence of finger loops 4, 6 has not only fully cocked the clip feeding mechinism, but has also resulted in the placement of a new clip 37 in the key position 125 so that it may be ready for later placement in jaw portions 32, 34.

Figure 11:
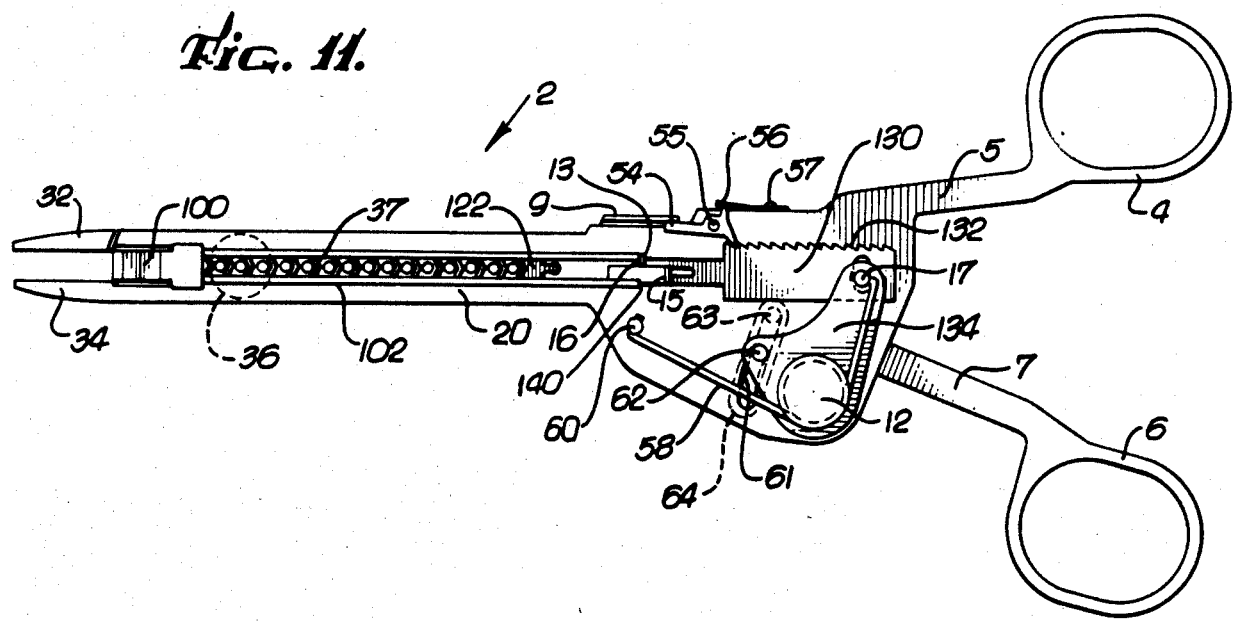
FIG. 11 is a side view of an alternate embodiment of the clip applicating device of the present invention.

An alternate embodiment of the spring activated hemostatic clip applicator 2 of the present invention is illustrated in FIG. 11. In a comparison of FIG. 11 with FIG. 1, it can be seen that the alternate embodiment illustrated in FIG. 11 is a simplified version of the instrument illustrated in FIG. 1. That is, the ratchet teeth 52 of the preferred embodiment have been transferred to the rearward-most section of feed blade 18 as serrations 132. Energy is still stored in ratchet spring 58 by the clockwise rotation of coupling 134, that rotation being imparted in the same manner as in the preferred embodiment via link 64. This clockwise rotation of coupling 134 is brought about by the inward movement of upper finger loop 4, and thus the rearward movement of feed blade 18. As in the preferred embodiment, during the cocking operation of the instrument, latch 54 is held in contact with the serrations 132 by the action of spring 56. Then, when a clip is to be loaded to the jaws 32, 34, a slight upward movement of upper finger loop 4 with respect to lower finger loop 6 will cause tab portion 9 to rotate latch 54 counter-clockwise about pivot 55. This counter-clockwise rotation of latch 54 disengages latch 54 from the serrations 132, thereby allowing spring 58 to rapidly move feed blade 18 through the main body 20 and into the jaws 32, 34.

It can be seen from the above description in conjunction with the associated illustrations, that the spring activated clip applying device 2 of the present invention provides an automatic and rapid feeding of hemostatic clips 37 into the jaws of the instrument 2. With only the slightest upward movement of finger loop 4, a clip is almost instantaneously delivered to the jaw portions 32, 34. Then, simply by moving finger loops 4 and 6 toward one another, a hemostatic clip 37 which has been loaded in the jaw portions 32, 34 can be deformed around a blood vessel or the like. Simultaneously with this crimping of the hemostatic clip 37, the instrument is again storing energy in a spring so that when another clip is needed, it can be readily available. This process of inward and outward movement of finger loops 4 and 6 may be repeated rapidly, so that one vessel after another is closed by hemostatic clips 37, until the supply of clips in magazine 102 is depleted.

Even with this additional feature of almost instantaneous loading of hemostatic clips, the clip applying device 2 of the present invention provides the further advantage of high visibility to the user. Because the device 2 is of an extremely thin design, essentially the width of currently used hemostats, and because jaw portions 32 and 34 are curved away from the main body 20, and finally because the clip feed blade 18 is divided into thin forked sections 21 at its extreme end, a surgeon using clip applying device 2 will have a clear view of the vessel he is closing.

There has been described herein a new an novel clip applying device which has special utility for applying hemostatic clips to blood vessels and the like. However, it is to be understood that various alternate embodiments using the principles of the present invention may be readily incorporated. Thus, while specific embodiments of the present invention have been disclosed and described in detail herein, it will be understood by those skilled in the art that various changes in form and detail may be made therein without departing from the spirit and scope of the invention.

We claim:

1. In a surgical clip applying device of the type having a main body, a clip magazine coupled to the main body for holding a plurality of clips, clip deforming means coupled to the main body for receiving and deforming said clips, clip feed means for moving said clips from the clip magazine to the deforming means, the improvement comprising, means for actuating said clip feed means including
   (i) two handle portions coupled to said main body; and
   (ii) energizing means coupled to said main body, said clip feed means and one said handle portion for storing energy and selectively supplying said energy to said clip feed means, wherein movement of one said handle portion with respect to the other said handle portion causes said energizing means to store energy and subsequent movement of one said handle portion with respect to the other said handle portion causes said energizing means to supply said energy to said clip feed means so as to cause one said clip to be moved rapidly from said clip magazine to said clip deforming means.

2. The clip applying device of claim 1 wherein said energizing means comprises a spring adapted to store energy and selectively couple said energy to said clip feed means.

3. The clip applying device of claim 2, wherein said energizing means further includes a ratchet member coupled to said clip feed means, said spring and said main body, wherein movement of one said handle portion with respect to the other said handle portion causes a displacement of said ratchet member and a corresponding storage of energy in said spring, and subsequent movement of one said handle portion with respect to the other said handle portion causes said spring and said ratchet member to supply said energy to said clip feed means.

4. The clip applying device of claim 3 wherein said energizing means further includes a latch coupled to said main body and adapted to engage said ratchet member, wherein said latch engages said ratchet member so as to prevent reverse movement while energy is stored in said spring and said latch is disengaged from said ratchet member when said energy is to be supplied to said clip feed means.

5. The clip applying device of claim 4 wherein said clip feed means is a blade member adapted to move longitudinally through said clip magazine, said blade member having a forked portion at the end nearest said clip deforming means, wherein during the contraction of said clip deforming means, said forked portion is also contracted.

6. The clip applying device of claim 5 wherein said blade member is comprised of a plurality of laminated strips adapted to move longitudinally relative to said main body while bending laterally.

7. The clip applying device of claim 1 wherein said clip feed means is a blade member adapted to move longitudinally through said clip magazine, said blade member having a forked portion at the end nearest said clip deforming means, wherein contraction of said clip deforming means to deform a clip also contracts said forked portion.

8. The clip applying device of claim 7 wherein said blade member is comprised of a plurality of laminated strips adapted to move longitudinally relative to said main body while bending laterally.

9. In a surgical clip applying device of the type having a main body, a clip magazine coupled to the main body for holding a plurality of clips, upper and lower jaw portions coupled to said main body and adapted to receive, maintain and deform a clip therebetween, a clip feed blade adapted to slide into said jaw portions so as to move said clips from said magazine to said jaw portions, an upper handle portion fixedly coupled to said main body, and a lower handle portion pivotally coupled to said main body and fixedly coupled to said clip deforming means, the improvement comprising:
   (i) a ratchet member coupled to said clip feed blade and said lower handle portion;
   (ii) a spring coupled to said main body and said ratchet member; and
   (iii) a latch coupled to said main body and adapted to engage said ratchet member, wherein movement of said lower handle portion toward said upper handle portion causes displacement of said ratchet member and storage of energy in said spring, and reverse movement of said ratchet member is prevented by engagement of said latch with said ratchet member until said upper handle portion is moved away from said lower handle portion a predetermined distance at which time said latch is disengaged from said ratchet member thereby allowing the energy stored in said spring to induce reverse movement of said ratchet member and the corresponding rapid sliding of said clip feed blade through said magazine and into said jaw portions, thereby rapidly moving one said clip into said jaw portions.

10. The clip applying device of claim 9 wherein said clip feed blade is a blade member adapted to move longitudinally through said clip magazine, said blade member having a forked portion at the end nearest said clip deforming means, wherein during the contraction of said jaw portions, said forked portion is also contracted.

11. The clip applying device of claim 10 wherein said blade member is comprised of a plurality of laminated strips adapted to move longitudinally relative to said main body while bending laterally.

12. In a surgical clip applying device of the type having a main body, a clip magazine coupled to the main body for holding a plurality of clips, upper and lower jaw portions coupled to said main body and adapted to receive, maintain and deform a clip therebetween, a clip feed blade adapted to slide through said magazine and into said jaw portions so as to move said clips from said magazine to said jaw portions, an upper handle portion fixedly coupled to said main body, and a lower handle portion pivotally coupled to said main body and fixedly coupled to said upper jaw portion, the improvement comprising:

(i) said clip feed blade having a plurality of serrations along a portion of one longitudinal edge nearest said handle portions;

(ii) a spring coupled to said clip feed blade and said main body; and (iii) a latch coupled to said main body and adapted to engage said clip feed blade serrations, whereby movement of said lower handle portion toward said upper handle portion causes a retraction of said clip feed blade away from said jaw portions and a corresponding distortion of said spring from its quiescent configuration, return of said clip feed blade is prevented by engagement of said latch with said clip feed blade serrations until said upper handle portion is moved away from said lower handle portion at which time said latch is disengaged from said serrations thereby allowing said spring to return to its quiescent configuration with a corresponding rapid sliding of said clip feed blade through said magazine and into said jaw portions, thereby rapidly moving one said clip into said jaw portions.

13. The clip applying device of claim 12 wherein said clip feed blade is a blade member adapted to move longitudinally through said clip magazine, said blade member having a forked portion at the end nearest said jaw portions, whereby during the contraction of said jaw portions, said forked portion is also contracted.

14. The clip applying device of claim 13 wherein said clip feed blade is comprised of a plurality of laminated strips adapted to move longitudinally relative to said main body while bending laterally.

15. In a surgical clip applying device of the type having a main body, a clip magazine coupled to the main body for holding a plurality of clips, clip deforming means coupled to the main body for receiving and deforming said clips, and clip feed means for moving said clips from the clip magazine to the deforming means, the improvement comprising:

energizing means coupled to said main body and said clip feed means for storing energy and supplying the stored energy to actuate the clip feed means;

latch means for latching the energizing means to retain the energy stored in the energizing means;

means adapted for manual operation for selectively actuating the latch means to release the energy stored in the energizing means, wherein the released energy is supplied to the clip feed means which causes the clip feed means to move a clip from the magazine to the deforming means; and means adapted for manual operation for restoring the energy in the energizing means;

wherein sequential clips, to the extent of said plurality of clips, may be fed to said deforming means for sequential application thereof.

16. The device of claim 15, wherein the energizing means comprises a spring adapted to store energy and supply the energy to the clip feed means.

17. The device of claim 15, wherein the means for actuating the latch means and the means for restoring the energy comprise two handle portion at least one of which is coupled to the main body wherein movement of one said handle portion with respect to the other said handle portion causes the energizing means to store energy which is retained by the latch means and a subsequent movement of one said handle portion with respect to the other said handle portion actuates the latch means which causes the energizing means to release and supply the energy to said clip feed means so as to cause a clip to be moved rapidly from the clip magazine to the clip deforming means.

18. In a surgical clip applying device of the type having a main body, a clip magazine coupled to the main body for holding a plurality of clips, clip deforming means coupled to the main body for receiving and deforming said clips, clip feed means for moving said clips from the clip magazine to the deforming means, and two handle portions coupled to the deforming means for actuating the deforming means as the handle portions are moved together; the improvement comprising, energizing means coupled to at least one handle portion and the clip feed means, for energizing the clip feed means to cause the clip feed means to move a clip from the magazine to the deforming means, said energizing means having means for storing energy as the handle portions are moved together to deform a clip, and means responsive to a subsequent movement of the handle portions away from each other, for releasing the stored energy to energize the clip feed means independent of further movement of the handle portions.

19. The device of claim 18 further comprising means for allowing the handle portions to be moved apart from each other a predetermined distance before the clip feed means is energized thereby allowing the handle portions to be opened and closed within the predetermined distance without energizing the clip feed means.

20. In a surgical clip applying device of the type having a main body, a clip magazine coupled to the main body for holding a plurality of clips, and opposing clip deforming jaws coupled to the main body for receiving and compressing the clips to deform the clips, the improvement comprising clip feed means for moving said clips from the clip magazine forward to the clip deforming jaws including:

a clip feed blade adapted to move longitudinally to the clip deforming jaws, said feed blade having a flexible forked portion at the end nearest the clip deforming jaws, which is adapted to engage a clip as the clip is moved to the deforming jaws and is further adapted to accommodate being compressed by the clip deforming jaws should the forked portion of the feed blade remain in the deforming jaws as a clip is deformed.

21. In a surgical clip applying device of the type having a main body, a clip magazine coupled to the main body for holding a plurality of clips, clip deforming means coupled to the main body for receiving and deforming the clips, clip feed means for moving the clips from the clip magazine to the deforming means and clip advancement means for advancing the clips through the magazine to the clip feed means, the improvement comprising:

energizing means coupled to the main body and the clip advancement means for storing energy and supplying the stored energy to actuate the clip advancement means;

latch means for latching the energizing means to retain the energy stored in the energizing means;

means adapted for manual operation for selectively actuating the latch means to release the energy stored in the energizing means, wherein the released energy is supplied to the clip advancement means which causes the clip advancement means to move the clips through from the magazine to the clip feed means; and means adapted for manual operation for restoring the energy in the energizing means;

wherein sequential clips, to the extent of said plurality of clips, may be advanced to the clip feed means.

22. The device of claim 21, wherein the energizing means comprises a spring adapted to store energy and supply the energy to the clip feed means.

23. The device of claim 21, wherein the means for actuating the latch means and the means for restoring the energy comprise two handle portions at least one of which is coupled to the main body wherein movement of one said handle portion with respect to the other said handle portion causes the energizing means to store energy which is retained by the latch means and a subsequent movement of one said handle portion with respect to the other said handle portion actuates the latch means which causes the energizing means to release and supply the energy to the clip advancement means so as to cause the clips to be moved through the clip magazine to the clip feed means.

24. In a surgical clip applying device of the type having a main body, a clip magazine coupled to the main body for holding a plurality of clips, clip deforming means coupled to the main body for receiving and deforming the clips, clip feed means for moving the clips from the clip magazine to the deforming means, clip advancement means for advancing the clips through the magazine to the clip feed means, and two handle portions coupled to the deforming means for actuating the deforming means as the handle portions are moved together; the improvement comprising, energizing means coupled to at least one handle portion and the clip advancement means, for energizing the clip advancement means to cause the clip advancement means to advance the clips through the magazine to the clip feed means, said energizing means having means for storing energy as the handle portions are moved together to deform a clip, and means responsive to a subsequent movement of the handle portions away from each other, for releasing the stored energy to energize the clip advancement means independent of further movement of the handle portions.

25. A surgical clip applying device comprising:

a first unitary member having a clip deforming jaw at one end and a finger loop at the other;

a second unitary member having a clip deforming jaw at one end and a finger loop at the other end, said first and second members being pivotally coupled together so that opening and closing the finger loops causes the jaws to open and close together to deform a clip placed therein;

a clip magazine coupled to at least one member for holding a plurality of clips;

a clip feed blade for moving a clip from the magazine to the member jaws;

actuator means coupled to the finger loops and the clip feed blade, for actuating the clip feed blade to thereby move a clip to the jaws as the finger loops are moved relative to each other; and lost motion means coupled to the actuator means and the finger loops, for allowing the finger loops to be moved relative to each other within a predetermined distance after a clip has been deformed in the jaws without actuating the clip feed blade wherein a clip in the jaws may be manipulated by relative movement of the finger loops within the predetermined distance without actuating the clip feed blade.

26. In a surgical clip applying device of the type having a main body, a clip magazine coupled to the main body for holding a plurality of clips, clip deforming means coupled to the main body for receiving and deforming said clips, a clip feed blade for moving said clips from the clip magazine to the deforming means, and two handle portions, at least one of which is coupled to the main body and the deforming means for actuating the deforming means as the handle portions are moved toward each other; the improvement comprising, means coupled to at least one handle portion for withdrawing the feed blade from the clip deforming means to the magazine as the handle portions are moved toward each other;

releasable latch means for latching the feed blade to prevent the feed blade from moving forward toward the deforming means until released;

means coupled to at least one handle portion for releasing the latch means when the handle portions have been opened a predetermined distance apart; and lost motion means for allowing the handle portions to be moved apart from each other within the predetermined distance without reversing the clip feed blade thereby allowing the handle portions to be opened within the predetermined distance to actuate the deforming means without actuating the clip feed blade.

27. In a surgical clip applying device of the type having a main body, a clip magazine coupled to the main body for holding a plurality of clips, clip deforming means coupled to the main body for receiving and deforming the clips, clip feed means for moving the clips from the clip magazine to the deforming means, clip advancement means for advancing the clips through the magazine to the clip feed means, and two handle portions coupled to the deforming means for actuating the deforming means as the handle portions are moved together; the improvement comprising:

energizing means coupled to at least one handle portion, the clip advancement means and the clip feed means, for energizing the clip feed means and clip advancement means to cause the clip advancement means to advance the clips through the magazine to the clip feed means and to cause the clip feed means to move a clip from the magazine to the clip deforming means, said energizing means having means for storing energy as the handle portions are moved together to deform a clip, and means responsive to a subsequent movement of the handle portions away from each other, for releasing the stored energy to energize the clip advancement means and clip feed means independent of further movement of the handle portions.

* * * * *